(12) United States Patent
Wong et al.

(10) Patent No.: US 7,367,213 B2
(45) Date of Patent: May 6, 2008

(54) APPARATUS FOR TESTING BENDING STRENGTH

(75) Inventors: Shih-Fang Wong, Guangdong (CN);
Wen-Haw Tseng, Guangdong (CN); Li Li, Guangdong (CN); Lei-Tong Yu, Guangdong (CN); Xiu-Xuan Li, Guangdong (CN); Yun-Tao Gao, Guangdong (CN)

(73) Assignees: Hong Fu Jin Precision Industry (Shen Zhen) Co., Ltd., Longhua Town, Bao'an District, Shenzhen, Guangdong Province (CN); Hon Hai Precision Industry Co., Ltd., Tu-Cheng, Taipei Hsien (TW)

( * ) Notice: Subject to any disclaimer, the term of this patent is extended or adjusted under 35 U.S.C. 154(b) by 0 days.

(21) Appl. No.: 11/679,188

(22) Filed: Feb. 27, 2007

(65) Prior Publication Data
US 2007/0209448 A1 Sep. 13, 2007

(30) Foreign Application Priority Data
Mar. 13, 2006 (CN) .......................... 2006 1 0034466

(51) Int. Cl.
*G01N 3/30* (2006.01)
(52) U.S. Cl. ..................................... 73/12.07; 73/12.06
(58) Field of Classification Search ................ 73/12.01, 73/12.04, 12.05, 12.06, 12.07, 798, 816, 73/825, 875, 849
See application file for complete search history.

(56) References Cited

U.S. PATENT DOCUMENTS

| | | | | | |
|---|---|---|---|---|---|
| 3,209,580 | A | * | 10/1965 | Colby | ........................ 73/12.06 |
| 3,600,932 | A | * | 8/1971 | Hill et al. | ................... 73/12.07 |
| 4,426,683 | A | * | 1/1984 | Kissell | ........................ 700/275 |
| 6,508,103 | B1 | * | 1/2003 | Shim et al. | ................ 73/12.06 |
| 6,892,564 | B2 | * | 5/2005 | Ishikawa | .................... 73/12.06 |

OTHER PUBLICATIONS

Goyal S., Buratynski E.K., "Methods for Realistic Drop-Testing" The International Journal of Microcircuits and Electronic Packaging, vol. 23, No. 1, First Quarter 2000.*

* cited by examiner

*Primary Examiner*—Edward Lefkowitz
*Assistant Examiner*—Punam Patel
(74) *Attorney, Agent, or Firm*—Winston Hsu

(57) ABSTRACT

An apparatus for testing bending strength is provided. The apparatus includes a frame, a motor, and a control part. The frame includes an impingement board. The motor includes a piston. A piston head is mounted on an end of the piston for impacting the impingement board. The piston head defines a space configured for receiving a hand-held device. The control part is for controlling the piston to move up and down repeatedly. The apparatus can be used to test a hand-held device's bending strength conveniently.

7 Claims, 3 Drawing Sheets

APPARATUS FOR TESTING BENDING STRENGTH

BACKGROUND

1. Technical Field

The present invention relates to an apparatus for testing bending strength, and particularly to an apparatus for testing hand-held device's bending strength.

2. General Background

Hand-held devices, such as mobile phones, media players, etc, are easily damaged by inadvertent pressing stress. For example, if a user of the hand-held device sits down or squats down with the hand-held device is in the trousers' pocket of the user, the hand-held device will be subjected to the pressing stress. If the hand-held device is not strong enough, a liquid crystal display or an antenna of the hand-held device may be damaged.

For reasons mentioned above, after a hand-held device prototype is created, it is necessary to perform a bending strength test on the hand-held device prototype before the hand-held device is mass produced.

Therefore, what is needed is an apparatus for testing hand-held device' bending strength.

SUMMARY

An apparatus for testing bending strength is provided. The apparatus includes a frame, a motor, and a control part. The frame includes an impingement board. The motor includes a piston. A piston head is mounted on an end of the piston for impacting the impingement board. The piston head defines a space configured for receiving a hand-held device. The control part is for controlling the piston to move up and down repeatedly.

Other advantages and novel features will be drawn from the following detailed description with reference to the attached drawing, in which:

DETAILED DESCRIPTION OF THE EMBODIMENT

Figure 1:
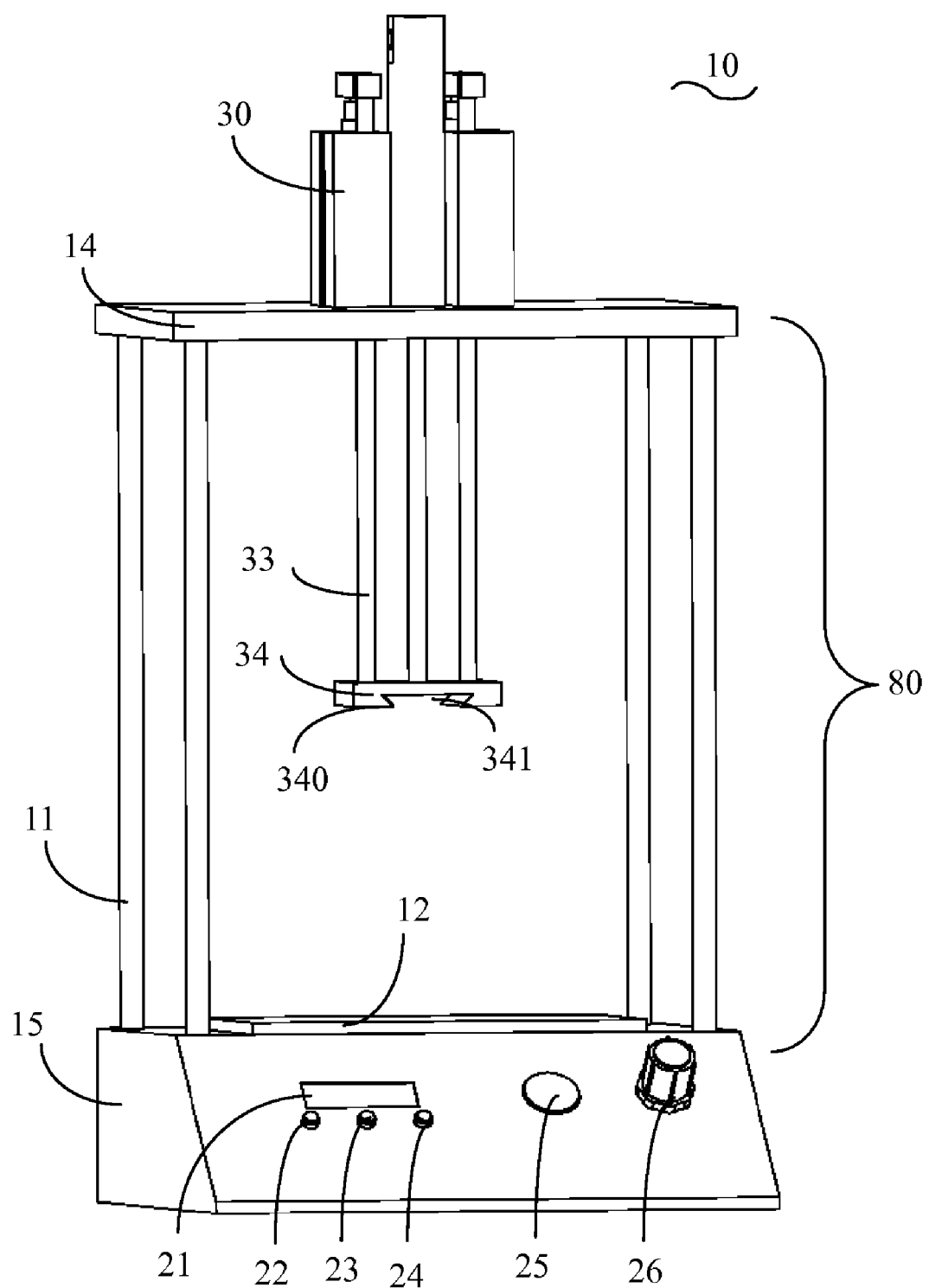
FIG. 1 is a schematic, solid view of an apparatus for testing bending strength according to a preferred embodiment of the present invention.
Figure 2:
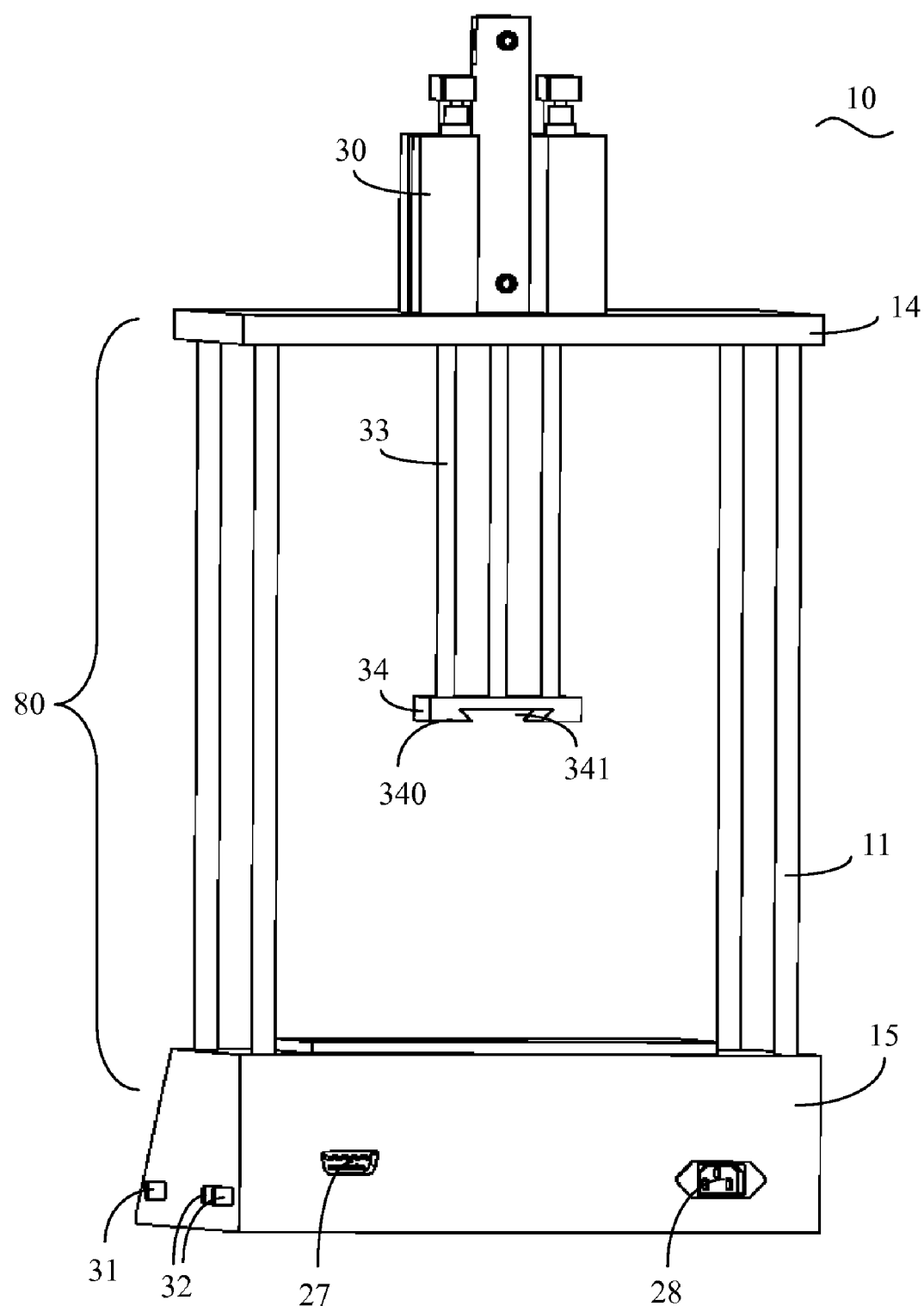
FIG. 2 is another schematic, solid view of the apparatus of FIG. 1.

Referring to FIGS. 1 and 2, an apparatus for testing bending strength is disclosed. The apparatus 10 includes a frame 80 and a motor 30. The frame 80 includes a base 15, a plurality of support beams 11, and a platform 14. In the embodiment of the present invention, the motor 30 is a pneumatic actuator. The pneumatic actuator 30 is mounted on the platform 14. A piston 33 of the pneumatic actuator 30 is constructed with three arms. A piston head 34 is mounted on the exposed end of the three arms of the piston 33. The piston head 34 includes a bottom surface 340. A space 341 is depressed in the bottom surface 340. In this embodiment of the present invention, the space 341 is a dovetail shaped cutout. The space 341 is configured for receiving a hand-held device that is wrapped in a flexible material. The flexible material is attached on an entrance of the space 341, and a part of the wrapped hand-held device is exposed outside the space 341. When the piston head 34 moves down and the bottom surface 340 impacts an impingement board 12 that is mounted on the base 15, the hand-held device wrapped in the flexible material is pushed into the space 341, deforming the flexible material. The hand-held device withstands bending forces generated by a combination of the flexible material and the impingement board 12.

An intake duct 31, two exhaust ducts 32, a manometer 25, and a regulator knob 26 are mounted on the base 15. The intake duct 31 and the exhaust ducts 32 are connected to an air pump (not shown). The manometer 25 indicates an air pressure of the pneumatic actuator 30. The regulator knob 26 regulates the air pressure in the pneumatic actuator 30. A display 21, input keys (e.g., an "enter" input key 22, an "up" input key 23, and a "down" input key 24), a power socket 28, and a communication port 27 are also positioned on the base 15. The display 21 shows parameters of the apparatus 10 (e.g., a target number of impacts, an impact frequency), and a test status (e.g., a number of impacts). The power socket 28 is used for connecting to a power supply (not shown). The communication port 27 can be an RS232 port. The communication port 27 is used to connect the apparatus 10 to a computer so as to transfer data between the apparatus and the computer. Data transfers include receiving control instructions from the computer.

Figure 3:
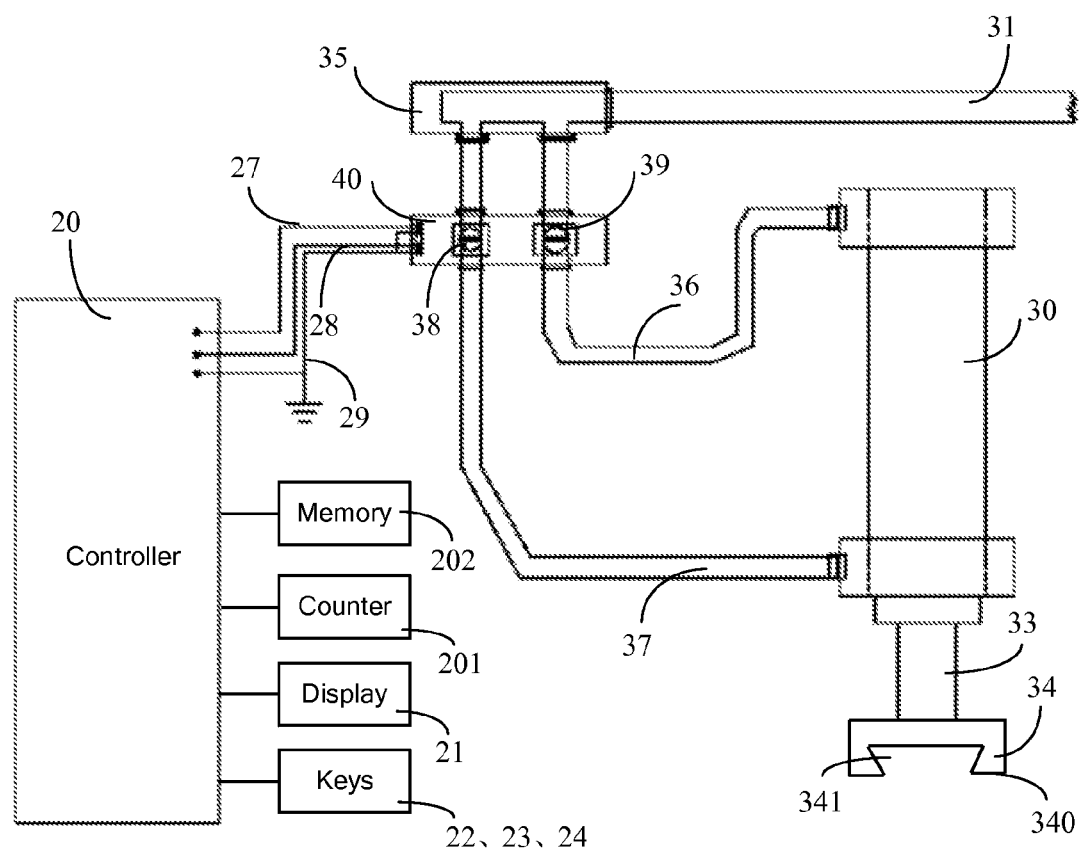
FIG. 3 is a schematic diagram of a hardware infrastructure of the apparatus of FIG. 1.

Referring to FIG. 3, a hardware infrastructure of the apparatus 10 is disclosed. A controller 20 and a valve controller 40 are positioned in the base 15. The controller 20 and the valve controller 40 control the pneumatic actuator 30, thus, driving the piston 33 to move up and down repeatedly. The controller 20 and the valve controller 40 are connected by three separate control wires 27, 28, 29. The control wire 29 further connects to earth. The valve controller 40 includes two valve switches 38, 39. Each of the valve switch 38 and the valve switch 39 is independently opened and closed by the controller. When the valve switch 38 is opened, air flows into the intake duct 31, a slide valve 35, the air pipe 37, and a first cylinder of the pneumatic actuator 30, retracting the piston head 34 up. If the valve switch 39 is opened, air flows into the intake duct 31, the slide valve 35, the air pipe 36, and a second cylinder of the pneumatic actuator 30, driving the piston head 34 outwards. When the valve switch 38/39 is closed, air in the pneumatic actuator 30 exhausts through the exhaust pipe 32. When the valve switches 38/39 are opened alternatively, the piston head 34 moves up and down repeatedly. The regulator knob 26 controls air pressure of the cylinders of the pneumatic actuator 30 through the valve controller 40, so as to control an impact power of the piston head 34.

The controller 20 is further connected to a memory 202, a counter 201, the display 21, and the input keys 22, 23, 24. The counter 201 includes a counter reset mechanism to start a count at zero. The counter 201 counts the number of impacts of the piston head 34 on the vessel 13. The memory 202 stores programs and parameters. The programs include an impact-executing program, and a parameter-setting program. The parameters include the impact frequency, and the target number of impacts. The input keys 22, 23, 24 are used to start or stop the impact-executing program and to set the parameters correspondingly. When the impact-executing program is run, the controller 20 controls the piston head 34 to move up and down repeatedly until the number of impacts equals to the target number of impacts or when a stop command is received from the input keys 22, 23, 24.

Although the present invention has been specifically described on the basis of a preferred embodiment and preferred method thereof, the invention is not to be construed as being limited thereto. Various changes or modifications may be made to the embodiment and method without departing from the scope and spirit of the invention.

What is claimed is:

1. An apparatus for testing bending strength, comprising:
   a frame comprising an impingement board;
   a motor comprising a piston and a piston head, the piston head mounted on the exposed end of the piston, comprising a surface configured for impacting with the impingement board and defining a space that is depressed in the surface configured for receiving a hand-held device;
   a flexible material attached at the entrance of the space, the flexible material configured for wrapping the hand-held device; and
   a control part for controlling the piston to move up and down repeatedly;
   wherein the flexible material becomes deformed when the surface is impacted with the impingement board.

2. The apparatus of claim 1, wherein the space is a dovetail shaped cutout.

3. The apparatus of claim 1, wherein the motor is a pneumatic actuator.

4. The apparatus of claim 3, wherein the control part comprises a controller and a valve controller, and the controller controls the valve controller to open or close.

5. The apparatus of claim 1, farther comprising input keys for respectively setting parameters and staffing/stopping a test.

6. The apparatus of claim 1, further comprising a display for showing a test result or parameters.

7. The apparatus of claim 1, further comprising a communication port configured for communicating with an external computer.

* * * * *